United States Patent [19]
Yoshikawa et al.

[11] Patent Number: 5,869,427
[45] Date of Patent: Feb. 9, 1999

[54] SUBSTITUTED THIOPHENE DERIVATIVE AND PLANT DISEASE CONTROL AGENT COMPRISING THE SAME AS ACTIVE INGREDIENT

[75] Inventors: Yukihiro Yoshikawa; Kanji Tomiya; Toshio Kitajima; Hiroyuki Katsuta; Osamu Takahashi, all of Chiba-ken; Shunichi Inami, Hokkai-do; Yuji Yanase, Chiba-ken; Naofumi Tomura, Chiba-ken; Junro Kishi, Chiba-ken; Hideo Kawasima, Chiba-ken, all of Japan

[73] Assignee: Mitsui Chemicals, Inc., Tokyo, Japan

[21] Appl. No.: 962,331

[22] Filed: Oct. 31, 1997

[30] Foreign Application Priority Data

Jun. 11, 1996 [JP] Japan ................... 8-293684

[51] Int. Cl.⁶ .................... C04D 333/22; A01N 43/10
[52] U.S. Cl. .................... 504/209; 549/59; 548/365.7; 548/214; 504/280; 504/269; 504/289
[58] Field of Search ..................... 504/209, 280, 504/269, 289; 549/59; 548/365.7, 214

[56] References Cited

FOREIGN PATENT DOCUMENTS

| 268892 | 6/1988 | European Pat. Off. . |
|---|---|---|
| 313091 | 4/1989 | European Pat. Off. . |
| 737682 | 10/1996 | European Pat. Off. . |
| 7196637 | 8/1995 | Japan . |

Primary Examiner—Johann Richter
Assistant Examiner—Laura R. C. Lutz
Attorney, Agent, or Firm—Burns, Doane, Swecker & Mathis, L.L.P.

[57] ABSTRACT

A novel substituted thiophene derivatives represented by the formula (1) in the invention:

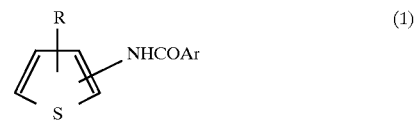

wherein R is a straight or branched alkyl group having 3–12 carbon atoms, straight or branched halogenoalkyl group having 3–12 carbon atoms, straight or branched alkenyl group having 3–10 carbon atoms, straight or branched halogenoalkenyl group having 3–10 carbon atoms, or cycloalkyl group having 3–10 carbon atoms, the cycloalkyl group being unsubstituted or substituted with an alkyl group having 1–4 carbon atoms, R and —NHCOAr are adjacent to each other, and Ar is a heterocyclic group; have excellent control activity on various plant disease such as Gray mold, Powdery mildew, Blast and Rust, and are useful as a plant disease control agent due to outstanding residual effect on *Botrytis cinerea* and excellent effect on *Gibberella zeae*.

16 Claims, No Drawings

SUBSTITUTED THIOPHENE DERIVATIVE AND PLANT DISEASE CONTROL AGENT COMPRISING THE SAME AS ACTIVE INGREDIENT

BACKGROUND OF THE INVENTION

1. Field of the Invention

The present invention relates to a novel substituted thiophene derivative and a plant disease control agent comprising the same as an active ingredient.

2. Description of the Related Art

The plant disease control agent which has been developed in recent years and has a selective activity differs from a conventionally used, nonselective plant disease control agent, and can exhibit steady effect at a low dosage. However, the new control agent has a problem of developing a resistant strain in repeated use and leading to reduction in efficacy.

For example, a benzimidazole-based fungicide has a wide fungicidal spectrum and also exhibits an excellent effect on *Botrytis cinerea*. However, such fungicide caused in 1970's a drastic reduction in efficacy due to appearance of a resistant fungus. A dicarboxyimide-based fungicide was focused attention as a replacement of the benzimidazole-based fungicide. Nevertheless a resistant fingus also appeared in the 1980's also against the dicarboxyimide-based fungicide. Consequently, the countermeasure for controlling the resistant *Botryrtis cinerea* has become a serious problem in the world.

On the other hand, an azole-based fungicide has a wide fungicidal spectrum and is an excellent pesticide which exhibits efficacy at a hitherto unexampledly low dosage particularly for powdery mildew and rust of various crops and also for scab of apple and pear. However, a resistant fungus against this pesticide has recently appeared and also led to a sharp reduction in the pesticide efficacy. The repeated use of the pesticide also tends to be restricted.

Thus, the appearance of the pesticide resistant fungus has become an inevitable problem for the selective plant disease control agent, and accordingly development of a new pesticide is now an urgent subject.

Many aromatic carboxylic acid anilide derivatives have been conventionally known to exert fungicidal activity. Recently, for example, Japanese Laid-Open Patent HEI 5-221994 and 6-199803 (European Patent A-545099 and A-58930 1) have described that various carboxylic acid anilide derivatives exhibit effect on *Botrytis cinerea*.

On the other hand, European Patent A-737682 has described fungicidal activity of a substituted thiophene derivative represented by the general formula:

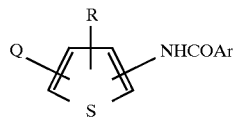

wherein Q is a hydrogen, fluorine, chlorine, bromine or iodine atom, or a methyl, trifluoromethyl, methoxy, methylthio, methylsulfoxy, methylsulfonyl, cyano, acetyl, nitro, alkoxycarbonyl or amino group; R is a straight or branched alkyl group having 1–12 carbon atoms, straight or branched halogenoalkyl group having 1–12 carbon atoms, straight or branched alkenyl group having 2–10 carbon atoms, straight or branched halogenoalkenyl group having 2–10 carbon atoms, alkylthioalkyl group having 2–10 carbon atoms, alkyloxyalkyl group having 2–10 carbon atoms, cycloalkyl group having 3–10 carbon atoms, halogenocycloalkyl group having 3–10 carbon atoms, or phenyl group having 1–3 substituents; substituent of phenyl group is a hydrogen or halogen atom or an alkyl group having 1–4 carbon atoms, alkenyl group having 2–4 carbon atoms, alkynyl group having 2–4 carbon atoms, cycloalkyl group having 3–6 carbon atoms, alkoxy group having 1–4 carbon atoms, halogenoalkoxy group having 1–4 carbon atoms, alkylthio group having 1–4 carbon atoms, alkylsulfoxy group having 1–4 carbon atoms, alkylsulfonyl group having 1–4 carbon atoms, cyano group, acyl group having 2–4 carbon atoms, alkoxycarbonyl group having 2–4 carbon atoms, amino or amino group substituted with alkyl group having 1–3 carbon atoms; R and —NHCOAr are adjacent to each other; and Ar is a group represented by the general formulas (B1l)–(B8);

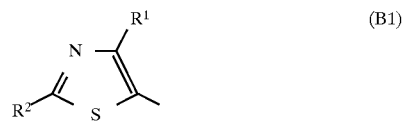

(B1)

(B2)

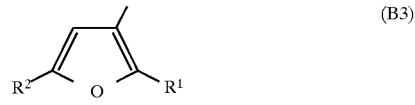

(B3)

(B4)

(B5)

(B6)

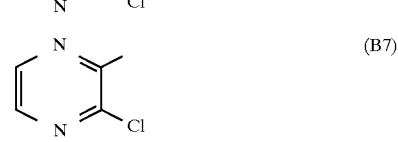

(B7)

(B8)

wherein $R^1$ is a chlorine, bromine or iodine atom, or a methyl, ethyl, difluoromethyl or tifluoromethyl group; $R^2$ is a hydrogen atom, or a methyl, trilluormethyl or amino group; and n is an integer of 0–2.

The present inventors have considered that the application field will be extended with a small lead on the environment if a pesticide having higher control activity and extended residual effect for a long period can be developed.

Consequently the object of the invention is to save labor and enhance safety for the environment by providing a plant

3 disease control agent having a wide fungicidal spectrum and long residual effect.

SUMMARY OF THE INVENTION

As a result of an investigation with deep interest on the physiological activity of various heterocyclic amine derivatives, the present inventors have found that a certain species of aninothiophene derivative has a higher control effect and longer residual effect than ever for various diseases, has high safety for crops and thus can fulfil the above object. Thus, the present invention has been completed.

That is, the aspect of the invention is a substited thiophene derivative represented by the formula(1):

wherein R is a straight or branched alkyl group having 3–12 carbon atoms, straight or branched halogenoalkyl group having 3–12 carbon atoms, straight or branched alkenyl group having 3–10 carbon atoms, straight or branched halogenoalkenyl group having 3–10 carbon atoms, or cycloalkyl group which has 3–10 carbon atoms and can be substituted with an alkyl group having 1–4 carbon atoms, R and —NHCOAr are adjacent to each other, and Ar is a heterocyclic group represented by the formulas (A1)–(A5):

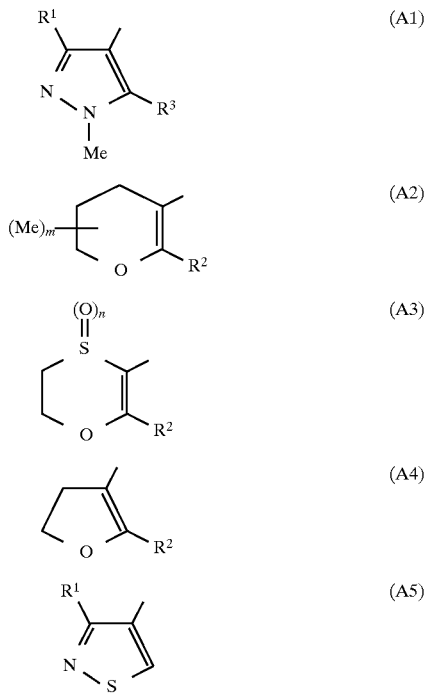

wherein $R^1$ is a trifluoromethyl group, difluoromethyl group, methyl group, ethyl group or halogen atom, $R^2$ is a methyl group, ethyl group, trriluoromethyl group or difluoromethyl group, $R^3$ is a halogen atom, methyl group or methoxy group, m is an integer of 0–1, and n is an integer of 0–2; and a plant disease control agent comprising said derivative as an active ingredient.

4

DETAILED DESCRIPTION OF THE INVENTIVE

The substituent R of the thiophene derivative represented by the formula (1) in the invention specifically includes an isopropyl, sec-butyl, tert-butyl, 1-methylbutyl, 1-methylhexyl, 1-ethylpropyl, 1,2-dimethylbutyl, 1,3-dimethylbutyl, 1-ethyl-3-methylbutyl, 1,2-dimethylhexyl, 1,3-dimethyloctyl, 3-methylbutyl, 3-methylpentyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 1-ethyl-3-methybutyl, 1-isopropylbutyl, 1-9sopropyl-3-methylbutyl, 1-methyl-2-cyclopropylethyl, n-butyl, n-hexyl group and other straight or branched alkyl groups having 3–12 carbon atoms; a 3-chloro-1-methylbutyl, 2-chloro-1-methylbutyl, 1-chlorobutyl, 3,3-dichloro-1-methylbutyl, 3-chloro-1-methylbutyl, 1-methyl-3-trifiuoromethylbutyl, 3-methyl-1-trifluoromethylbutyl group and other straight or branched halogenoalkyl groups having 3–12 carbon atoms; a propenyl, 1-methyl-1-propenyl, 1-ethyl-1-butenyl, 2,4-dimethyl-1-pentenyl, 2,4-dimethyl-2-pentenyl group and other straight or branched alkenyl groups having 3–10 carbon atoms; a 2-chloro-1-methyl-1-butenyl group and other straight or branched halogenoalkenyl groups having 3–10 carbon atoms; and a cyclopropyl, cyclohexyl, 3-methylcyclopentyl, 3-methylcyclohexyl, 2-ethylcylclooctyl, 2-isopropylcyclodecyl group and other cycloalkyl groups having 3–10 carbon atoms which are unsubstituted or substituted with an alkyl group having 1–4 carbon atoms.

The substituent R of the thiophene derivative represented by the formula (1) in the invention is preferably a straight or branched alkyl group having 5–7 carbon atoms and more preferably 1,3-dimethylbutyl and 3-methylbutyl group.

Exemplary Ar includes a 1-methyl-4-pyrazolyl group which is substituted with a trifluoromethyl, difluoromethyl, methyl or ethyl group or halogen atom at the 3-position and a halogen atom, or methyl or methoxy group at the 5-position, for example, 5-chloro-1,3-dimethyl-4-pyrazolyl, 1,5-dimethyl-3-difluoromethyl-4-pyrozolyl, and 5-fluoro-1-methyl-3-iodo-4-pyrazolyl group; a 3,4-dihydro-2H-pyran-5-yl group which is substituted with a trilluoromethyl, difluoromethyl, methyl or ethyl group at the 6-position and unsubstituted or substituted with a methyl group at the 2, 3 or 4-position, for example, 6-methyl-3,4-dihydro-2H-pyran-5-yl group; a 2,3-dihydro-1,4-oxathiine-5-yl group which is substituted with a trifluoromethyl, difluoromethyl, methyl or ethyl group at the 6-position, for example, 6-methyl-2,3-dihydro-1,4-oxathiine-5-yl group; a 2,3-dihydro-1,4-oxathiine-4-oxide-5-yl group which is substituted with a trifluoromethyl, difluoromethyl, methyl or ethyl group at the 6-position, for example, 6-methyl-2,3-dihydro-1,4-oxathiine-4-oxide-5-yl group; a 2,3-dihydro-1,4-oxathiine-4,4-dioxide-5-yl group which is substituted with a trifluoromethyl, difluoromethyl, methyl or ethyl group at the 6-position, for example, 6-methyl-2,3-dihydro-1,4-oxathiine-4,4-dioxide-5-yl group; a 2,3-dihydrofaran-4-yl group which is substituted with a trifluoromethyl, difluoromethyl, methyl or ethyl group at the 5-position, for example, 5-methyl-2,3-dihydrofuran-4-yl group; and an isothiazole-4-yl group which is substituted with a trifluoromethyl, difluoromethyl, methyl or ethyl group or halogen atom at the 3-position, for example, 3-methylisothiazole-4-yl and 3-trifluoromethylisothiazole-4-yl groups.

Preferred substituted thiophene derivatives are compounds wherein R is 1,3-dimethylbutyl or 3-methylbutyl group and Ar is (A1) wherein $R^1$ is methyl group and $R^3$ is a halogen atom, Ar is (A2) wherein $R^2$ is methyl or ethyl group and m is 0, Ar is (A3) wherein $R^2$ is methyl group and n is 0, or Ar is (A4) wherein R2 is methyl group.

More preferred substituted thiophene derivative is the compound wherein R is 1,3-dimethylbutyl or 3-methylbutyl group Ar is (A2) wherein $R^2$ is methyl group and m is 0.

The substituted thiophene derivative represented by the formula (1) in the invention is a novel compound and can be prepared by a process which is similar to a known process and is shown by the reaction formula below. That is, substituted aminothiophene represented by the formula (2) is reacted with carbonyl halide represented by the formula (3) in a molten state or in a solvent (reaction formula 1). Alternatively, substituted aminothiophene represented by the formula (2) is reacted with carboxylate ester represented by the formula (4) in a solvent in the presence of trimethylaluminum (reaction formula 2).

Reaction Formula 1

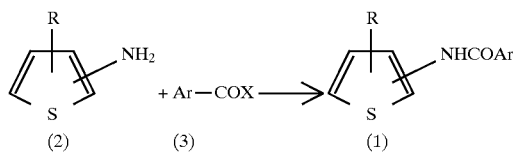

Reaction Formula 2

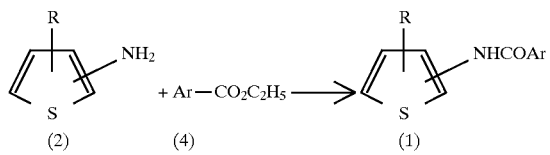

wherein R and Ar are the same as above, and X is a chlorine, bromine or iodine atom.

The reaction formula (1) will be illustrated. Representative solvents which can be used for the reaction are inert in the reaction and include, for example, hexane, petroleum ether and other aliphatic hydrocarbons; benzene, toluene, chlorobenzene, anisole and other aromatic hydrocarbons; dioxane, tetrahydrofuran, diethyl ether and other ethers; acetonitrile, propionitrile and other nitriles; ethyl acetate and other esters; dichloromethane, chloroform, 1,2-dichloroethane and other halogenated hydrocarbons; and dimethylformamide, dimethyl sulfoxide, and other aprotic solvents. The solvents can also be used as a mixture.

The reaction can also progress in the presence of a base. The bases which can be used include, for example, sodium hydroxide, potassium hydroxide, calcium hydroxide and other hydroxide of alkali and alkali earth metals; calcium oxide, magnesium oxide and other oxide of alkali and alkali earth metals; sodium hydride, calcium hydride and other hydride of alkali and alkali earth metals; lithium amide, sodium amide and other amide of alkali metals; sodium carbonate, potassium carbonate, calcium carbonate, magnesium carbonate and other carbonate of alkali and alkali earth metals; sodium hydrogen carbonate, potassium hydrogen carbonate and other hydrogen carbonate of alkali and alkali earth metals; methyllithium, butyllithium, phenyllithium and other alkali-metal alkyl; methylmagnesium chloride and other alkylmagnesium halide; sodium methoxide, sodium ethoxide, potassium t-butoxide, magnesium dimethoxide and other alkoxide of alkali and alkali earth metals; and triethylamine, pyridine, N,N-dimethylaniline, N-methylpiperidine, lutidine, 4-dimethylaminopyridine and other various organic bases. Triethylamine and pyridine are preferred in particular. No particular limitation is imposed upon the amount of these bases. The amount used is preferably 5–20mol % in excess of carbonyl halide, represented by the formula (3).

Substituted aminothiophene represented by the above formula (2) and carbonyl halide represented by the formula (3) are generally reacted in an equimolar amount. One reactant is sometimes used in 1–20mol % excess of the other reactant in order to improve the yield.

The reaction temperature is usually −20°–150° C., preferably 0°–40° C.

No particular restriction is put upon the reaction time. The reaction time is usually 0.5–5 hours.

Next, the reaction formula (2) will be illustrated. Solvents which can be used for the reaction are inert in the reaction and include, for example, hexane, petroleum ether and other aliphatic hydrocarbons; benzene, toluene, chlorobenzene, anisole and other aromatic hydrocarbons; dioxane, tetrahydrofuran, diethyl ether and other ethers; acetonitrile, propionitrile and other nitriles; dichloromethane, chloroform,1,2-dichloroethane and other halogenated hydrocarbons; and dimethyl sulfoxide and other aprotic solvents. These solvents can also be used as a mixture.

The reaction is usually carried out in the presence of a base. Exemplary bases which can be used include, for example, sodium hydroxide, potassium hydroxide, calcium hydroxide and other hydroxide of alkali and alkali earth metals; calcium oxide, magnesium oxide and other oxide of alkali and alkali earth metals; sodium hydride, calcium hydride and other hydride of alkali and alkali earth metals; lithium amide, sodium amide and other amide of alkali metals; sodium carbonate, potassium carbonate, calcium carbonate, magnesium carbonate and other carbonate of alkali and alkali earth metals; sodium hydrogen carbonate, potassium hydrogen carbonate and other hydrogen carbonate of alkali and alkali earth metals; trimethylaluminum, triethylaluminum and other trialkylaluminum; sodium methoxide, sodium ethoxide, potassium t-buthoxide, magnesium dimethoxide and other alkoxide of alkali and alkali earth metals; and triethylamine, pyridine, N,N-dimethylaniline, N-methylpiperidine, lutidine, 4-dimethylaminopyridine and other various organic bases. Thmethyl-aluminum is particularly preferred.

No particular limitation is imposed upon the amount of these bases. The amount is preferably in 5–200mol % excess of substituted aminothiophene represented by the formula (2).

Substituted aminothiophene represented by the above formula (2) and carboxylate ester represented by the formula (4) are generally reacted in an equimolar amount. One reactant is sometimes used in 1–100mol % excess of the other reactant in order to improve the yield.

The reaction temperature is usually −20°–150° C., preferably 0°–80° C.

No particular restriction is imposed upon the reaction time. The reaction time is usually 0.5–24 hours.

Next, synthetic process of the intermediate compound represented by the formula (2) in the invention will be illustrated.

1) Synthesis of 2-substituted-3-aminothiophene.

These compounds can be prepared, for example, by the process shown in the reaction formula (3) below. However, no restriction is imposed upon these processes.

(Process A):

2-Substituted-3-oxotetrahydorothiophene is converted to oxime by reacting with hydroxylamine hydrochloride in ethanol in the presence of barium hydroxide and successively treated with hydrogen chloride in ethyl ether to prepare amine (U.S. Pat. No. 4,317,915 and J. Org. Chem., 52, 2611(1987)).

(Process B-1 and B-2):

2-Acyl-3-aminothiophene is obtained by condensation of mercaptoacetone with α-chloroacrylonitrile (Process B-1, Synth. Commun., 9, 731(1979)), or by acylation of 3-acetylaminothiophene with acyl chloride in the presence of anhydrous aluminum chloride and successive hydrolysis (Process B-2, Bull. soc. chim. Fr., 1976, 151). 2-Acyl-3-aminothiophene thus obtained is protected with a t-butyloxycarbonyl group by using di-t-butyl dicarbonate in the presence of triethylamine, alkylated with an alkylating agent such as Grignard's reagent, and successively reduced with triethylsilane in trifluoroacetic acid to prepare amine.

(Process C and Process D):

3-Aminothiophene-2-carboxylic acid ester is protected with a t-butyloxycarbonyl group by using di-t-butyl dicarbonate in the presence of triethylamine, alkylated with an alkylating agent such as Grignard's reagent, and successively reduced with triethylsilane in trifluoroacetic acid to prepare amine.

Reaction Formula (3)
A process

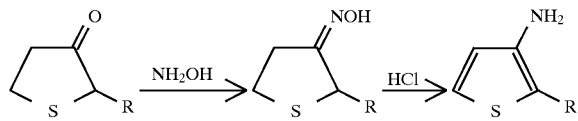

B-1 process

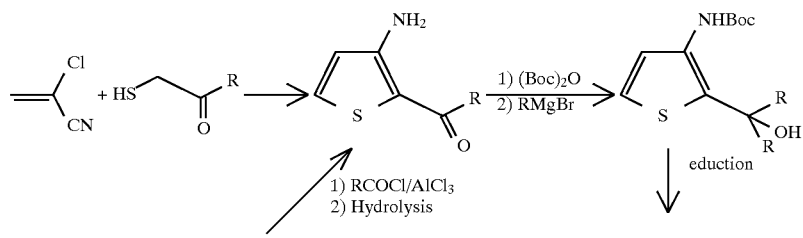

B-2 process

C process

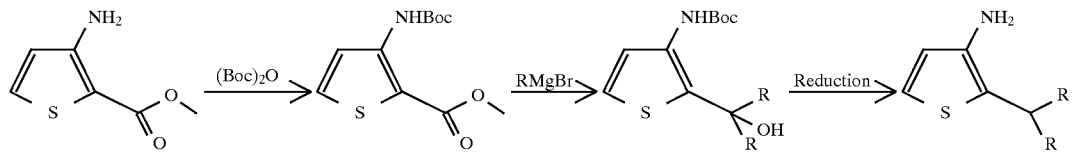

D process

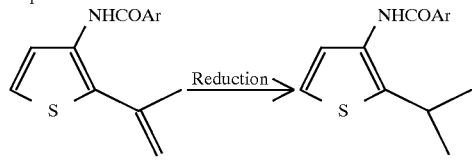

wherein R is the same as above.

The compound represented by the formula (1) in the invention can be prepared from 2-substituted-3-aminothiophene by way of the above processes. Further, 3-acylamino-2-alkylthiophene can be prepared by direct reduction of 3-acylamino-2-alkenyl substituted thiophene as shown in the process D.

2) Synthesis of 4-alkyl-3-aminothiophene (Process E):

These compounds can be prepared by the process shown in the reaction formula (4) below.

That is, 3-oxotetrahydrothiophene-4-carboxylic acid ester (U.S. Pat. No. 4,317,915 and J. Org. Chem., 52, 2611(1987)) is alkylated with alkyl halide in the presence of potassium carbonate and followed by hydrolysis and decarboxylation to obtain 3-oxotetrahydrothiophene. 3-Oxotetrahydrothiophene thus obtained is converted to oxime with hydroxylamine hydrochloride in ethanol in the presence of barium hydroxide and successively treated with hydrogen chloride in ethyl ether to prepare 4-alkyl-3-aminothiophene.

Reaction Formula (4)
E process

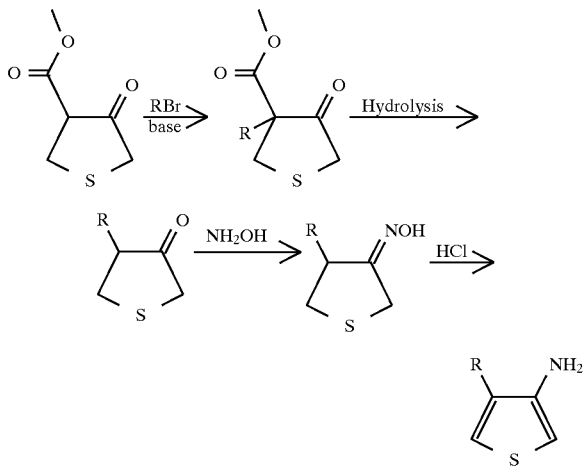

wherein R is the same as above.

The compound represented by the formula (1) in the invention can be prepared from 4-alkyl-3-aminothiophene thus obtained.

However, no restriction is imposed upon these processes.

The compound represented by the formula (1) in the invention and the plant disease control agent which comprising the same as an active ingredient always exhibit an excellent activity on rice diseases such as Blast(*Pyricularia oryzae*), Sheath blight(*Rhizoctonia solani*), Heliinthosporium leaf spot(*Cochliobolus miyabeanus*) and "Bakanae" disease(*Gibberela fujikuroi*), wheat diseases such as Powdery mildew (*Erysiphe graminis* f.sp.*hordei;* f.sp.*tritici*), Stripe rust(*Pucinia striiformis; P. graminis; P. recondita; P. hordei*), Leaf stripe(*Pyrenophora graminea*), Net blotch (*Pyrenophora teres*), Fusarium blight(*Gibberella zeae*), Snow rot (Typhula sp.; *Micronectriella nivalis*), Loose smut (*Ustilago tritici; U.nuda*), Eye spot(*Pseudocercosporella herpotrichoides*), Rhynchosporium leaf blotch (*Rhynchosporium secalis*), Septoria leaf blotch(*Septoria tritici*) and Glume blotch(*Leptosphaeria nodorum*), gray mold(*Botrytis cinerea*) of kidney beans, cucumber, tomato, strawberry, grape, potato, soybean, cabbage, Japanese eggplant and lettuce, Rust(*Phakopsora ampelopsidis*), Powdery mildew (*Uncinula necator*), Anthracnose)*Elsinoe ampelina*) and Ripe rot(*Glomerella cingulata*) of grape, Powdery mildew(*Podosphaera leucotricha*), Scab (*Venturia inaequalis*), Alternaria leaf spot(*Alternaria mali*), Rust (*Gymnosporangium yamadae*), Blossom blight(*Scleroinia mali*) and Canker (*Valsa mali*) of apple, Black spot (*Alternaria kikuchiana*), Scab(*Venturia nashicola*), Rust (*Gymnosporangium haraeanum*) and Physalospora canker (*Physalospora piricola*) of pear, Brown rot(*Sclerotinia cinerea*), Scab (*Cladosporium carpophilum*) and Phomopsis rot (Phomopsis sp.) of peach, Anthracnose(*Gloeosporium kaki*), Angular leaf spot(*Cercoapora kaki; Mycosphaerella nawae*) and Powdery mildew(*Phyllactinia kakikora*) of persimmon, Powdery mildew(*Sphaerotheca fuliginea*), Anthracnose (*Colletotrichum lagenarium*) and Gummy stem blight(*Mycosphaerella melonis*) of melon, Early blight (*Alternaria solani*) and leaf mold (*Cladosporium fulvam*) of tomato, Powdery mildew(*Erysiphe cichoracoerum*) Mycovellosiella leaf spot(*Mycovellosiella nattrassii*) of Eggplant, Alternaria leaf spot(*Alternaria japonica*) and White spot (*Cerocosporella barassicae*) of brassicaceae, Rust(*Puccinia allii*) and Alternaria leaf spot(*Alternaria porri*) of leek, Purple speck(*Cercopora kikuchii*), Sphaceloma scab (*Elsinoe glycinnes*) and Pod and stem blight (*Diaporthe phaseololum*) of soybean, Anthracnose(*Colletotrichum lindemuthianum*) of kidney beans, Leaf spot (*Mycosphaerella personatum*), and Brown leaf spot (*Cercospora arachidicola*) of peanut, Powdery mildew (*Erysiphe pisi*) of pea, Early blight(*Alternaria solani*) and black scurf (*Rhizoctonia solani*) of potato, Net blister blight (*Exobasidium reticulatum*), White scab(*Elsinoe leucospila*) and Anthracnose(*Colletotrichum theae-sinensis* of tea, Brown spot(*Alternaria longipes*), Powdery miidew (*Erysiphe cichoracearum*), and Anthracnose(*Colletotrichum tabacum*) of tobacco plant, Cercospora leaf spot(*Cercospora beticola*) of beat, Black spot(*Diplocarpon rosae*) and Powdery mildew(*Sphaerotheca pannosa*) of rose, Leaf blotch (*Septoria chrysanthemi-indici*) and Rust(*Puccinia horiana*) of chrysanthemum, Powdery mildew(*Sphaerotheca humuli*) of strawberry, Sclerotinia rot(*Sclerotinia sclerotiorum*) of soybean, melon, cucumber, strawberry, grape, potato, kidney beans, cabbage, Japanese eggplant and lettuce, Pod and stem blight(*Diaporthe citri*) of citrus and leaf bright (*Alternaria dauci*) of carrot.

Particularly, compounds represented by the general formula (1) of the invention have more excellent activity against Gray mold(*Botrytis cinerea*), Powdery mildew (*Sphaerotheca fuliginea*) of melon, Stripe rust(*Puccinia striiformis; P. graminis; P. recondita; P. hordei*) of cereals and some of compounds of the invention have more excellent residual activity for gray mold and more excellent efficacy against stripe rust.

Further, the compound represented by the formula (1) in the invention has possibility to be effective against *Trichophyton metagrophytes, T. rubrum, T. violaceum* and other Tricophyton microorganism; *Microsparum gpseum, M. canis* and other Microsparum microorganism; *Cndida albicans, C. tropicalis, C. kefyr, C. parapsilosis, C. krusei, C. guiliermondii, C. globrata* and Candida microorganism; *Cryptococcus neoformas* and Cryptococcus microorganism; *Spororia Schenckii* and other Sporotrichum; and *Epidermophyton floccosum*.

The term "carrier" means a synthetic or natural, inorganic or organic material which is formulated in order to assist reach of the effective ingredient to the portion to be treated and also to make storage, transport and handling of the effective ingredient compound easy. Any solid or liquid material can be used for the carrier so long as the materials commonly used for agricultural and horticultural formulations. No particular restriction is imposed on the carrier.

Solid carriers which can be used include, for example, montmorillonite, kaolinte and other clays; diatomaceous earth, China clay, talc, vermiculite, gypsum, calcium carbonate, silica gel, ammonium sulfate and other inorganic materials; soy bean powder, saw dust, wheat powder and other plant organic materials and urea.

Exemplary liquid carriers include toluene, xylene, cumene and other aromatic hydrocarbons; kerosene, mineral oil and other paraffine hydrocarbons; acetone, methyl ethyl ketone and other ketones; dioxane, diethylene glycol dimethyl ether and other ethers; methanol, ethanol, propanol, ethylene glycol and other alcohols; dimethylformamide, dimethyl sulfoxide and other aprotic solvents; and water.

In order to firther enhance the effect of the plant disease controlling agent in the invention, following adjuvant can also be used singly or as a mixture depending upon the object in view of the formulation and application place. Adjuvants which can be used include surfactants and binders which are commonly used for plant disease controlling agent, for example, ligninsulfonic acid, alginic acid, polyvinyl alcohol, gum arabic and sodium CMC, and stabilizers, for example, phenol compounds, thiol compounds and higher fatty acid ester for oxidation inhibition, phosphoric acid salts for pH regulation and light stabilizers in some cases. These adjuvants can be used singly or in combination, when needed. Further, an industrial fungicide or a bacteria proofing agent can also be added in a certain case in order to inhibit fungus and bacteria.

The adjuvants will be illustrated further in detail. Exemplary adjuvants which can be used for the purpose of emulsification, dispersion, spreading, wetting, binding and stabilization include salt of ligninsulfonic acid, salt of alkylbenzenesulfonic acid, ester salt of alkylsulfate, polyoxyalkylenealkylsulfate, ester salt of polyoxyalkylenealkylphosphate and other anionic surface active agents; polyoxyalkylene alkyl ether, polyoxalkylene alkyl aryl ether, polyoxyalkylene alkylamine, polyoxyalkylene alkylamide, polyoxyalkylene alkyl thioether, polyoxyalkylene fatty acid ester, glycerin fatty acid ester, sorbitan fatty acid ester, polyoxyalkylenesorbitan fatty acid ester, polyoxypropylene-polyoxyethylene block copolymer and other nonionic surface active agents; calcium stearate, wax and other lubricants, isopropyl hydrogen phosphate and other stabilizers; and other miscellaneous materials such as methylcellulose, carboxymethylcellulose, casein and gum arabic. However, no restriction is imposed upon these adjuvants. The content of the compound represented by the general formula (1) in the plant disease controlling agent of the invention differs depending upon formulation and is usually 0.05–20% by weight in the powder formulation, 0.1–80% by weight in the wettable powder, 0.1–20% by weight in the granule, 1–50% by weight in the emulsifiable concentrate, 1–50% by weight in the flowable formulation, and 1–80% by weight in the dry flowable formulation. Preferred concentration is 0.5–5% by weight in the powder formulation, 5–80% by weight in the wettable powder, 0.5–8% by weight in the granule, 5–20% by weight in the emulsifiable concentrate, 5–50% by weight in the flowable formulation and 5–50% by weight in the dry flowable formulation.

The content of adjuvants is 0–80% by weight and the content of the carrier is quantity obtained by subtracting the total content of the active ingredient compound and the adjuvants from 100% by weight.

The methods for applying the composition of the invention include seed disinfection and foliage application. However, the composition can exhibit satisfactory activity by any application method utilized by these who are skilled in the art.

Application rate and application concentration, are variant depending upon object crops, object diseases, abundance of disease damage, formulation of compound, application method and various environmental conditions. The amount of active ingredient is usually 50–1000 g/hectare, preferably 100–500 g/hectare in spraying. When a wettable powder, flowable formulation or emulsifiable concentrate is diluted with water and sprayed, the dilution is usually 200–20,000 times, preferably 1,000–5,000 times.

The plant disease controlling agent of the invention can of cause be used in combination with other fungicides, insecticides, herbicides, plant-growth regulators and other agricultural chemicals; soil conditioners; or materials having fertilizer effect. A mixed formulation of the fungicide in the invention can also be prepared by using these materials.

Exemplary other fungicides include triadimefon, hexaconazole, prochloraz, triilumizole, myclobutanil, epoxyconazole, flusilazole, propiconazole, tebuconazole and other azole fungicides; metalaxyl, oxadixyl and other acyl alanine fungicides; thiophanate-methyl, benomyl and other benzimidazole fungicides; manzeb and other dithiocarbamate fungicides; procymidone, iprodione and other dicarboxamide fungicide; tridemorph and other morphorine fungicide; flutolanil, pencycuron and other amide-based fungicide; fosetyl, tolclofos-methyl, DIBP, EDDP and other organophosphate fungicide; captan, TPN, PCNB and other organochlorine fungicide; and sulphur, kresoxim-methyl, azoxystrobin and other acrylate fungicide; mepanipyrim and other anilinopyrimidine fungicide, tricyclazole, probenazole, fluazinam, hymexazole, quinomethionate, flusulfamide, ferimzone, pyroquilon, iminoctadine-triacetate, iminoctadine-albesilate and other fungicide.

Insecticides include, for example, fenitrothion, daiazinon, pyridafenthion, chlorpyrfos, marathon, phenthoate, dimethoate, methyl thiometon, prothiofos, DDVP, acephate, EPN and other organophosphate insecticides; NAC, MTMC, BPMC, piicarb, benfracarb, carbosulfan, methomyl and other carbamate insecticides; and ethofenprox, cycloprothrin, permethrin, fenvalerate and other pyrethroid insecticides, cartap and other nereistoxin insecticides and imidacloprid and other nitromethylene insecticides. However, no restriction is imposed upon these materials.

EXAMPLE

The compounds of the invention will hereinafter be illustrated in detail by way of examples.

Example 1

Synthesis of N-[2-(1,3-dimethylbutyl)-3-thienyl]-5-chloro-1,3-dimethylpyrozole-4-carboxamide (Compound No. 1.11)

In an ice bath, 0.4 g of 3-amino-2-(1,3-dimethylbutyl) thiophene was dissolved in 3.0 g of pyridine. A solution containing 0.42 g of 5-chloro-1,3-dimethylpyrazole-4-carbonyl chloride in 3 ml of methylene chloride was dropwise added with stirring to the above obtained solution.

After stirring at 3° C. for an hour, the reaction mixture was poured into an 1N aqueous hydrochloric acid solution and extracted with ethyl acetate. The organic layers was washed with saturated aqueous sodium hydrogen carbonate solution and successively with a saturated aqueous sodium chloride solution, and dried over anhydrous sodium sulfate. The solvent was distilled off under reduced pressure and the residue was purified by silica gel chromatography. The desired product obtained was 0.41 g. Brown oil. The yield was 55%.

Example 2

Synthesis of N-[2-(1,3-dimethylbutyl)-3-thienyl]-5-chloro-3-trifluoromethyl-1-methylpyrazole-4-carboxamide (Compound No. 1. 10)

In an ice bath, 0.50 g of 3-amino-2-(1,3-dimethylbutyl) thiophene was dissolved in 3.0 g of pyridine. A solution containing 0.67 g of 5-chloro-3-trifluoromethyl-1-methylpyrazole-4-carbonyl chloride in 3 ml of methylene chloride was dropwise added with stirring to the above obtained solution.

After stirring at 3° C. for 2 hours, the reaction mixture was poured into an 1N aqueous hydrochloric add solution and extracted with ethyl acetate. The organic layers was washed with saturated aqueous sodium hydrogen carbonate solution and successively with a saturated aqueous sodium chloride solution, and dried over anhydrous sodium sulfate. The solvent was distilled off under reduced pressure. The residue was purified by silica gel chromatography to obtain 0.15 g of the desired product as brown oil. The yield was 14%.

Example 3

Synthesis of N-[2-(1,3-imethylbutyl)-3-thienyl]-5-chloro-3-ethyl-1-methylpyrazole-4-carboxamide (Compound No. 1.42)

In an ice bath, 1.50 g of 3-amino-2-(1,3-dimethylbutyl) thiophene was dissolved in 7.0 g of pyridine. A solution containing 1.70 g of 5-chloro-3-ethyl-1-methylpyrazole-4-carbonyl chloride in 10 ml of methylene chloride was dropwise added with stirring to the above obtained solution.

After stirring at 3° C. for an hour, the reaction mixture was poured into an 1N aqueous hydrochloric acid solution and extracted with ethyl acetate. The organic layers was washed with saturated aqueous sodium hydrogen carbonate solution and successively with a saturated aqueous sodium chloride solution, and dried over anhydrous sodium sulfate. The solvent was distilled off under reduced pressure. The residue was purified by silica gel chromatography to obtain 1.61 g of the desired product as a light brown crystal. The yield was 56%.

Example 4

Synthesis of N-[2-(1,3-dimethylbutyl)-3-thienyl]-6-methyl-3,4-dihydro-2H-pyran-5-carboxamide (Compound No. 1.7)

In a nitrogen atmosphere, 0.5 g of 3-amino-2-(1,3-dimmethylbutyl)-thiophene was dissolved in 5 ml of methylene chloride and 2 ml of a 15% toluene solution of trimethylaluminium was dropwise added with stirring to the above obtained solution. After stiring for 10 minutes, a solution containing 0.5 g of ethyl 6-methyl-3,4-dihydro-2H-pyran-5-carboxylate in 3 ml of methylene chloride was dropwise added.

After stirring at room temperature for 12 hours, the reaction mixture was poured into a 5% aqueous hydrochloric acid solution and extracted with ethyl acetate. The organic layers was washed with a 5% aqueous hydrochloric acid solution, saturated carbonate solution and successively saturated aqueous sodium chloride solution, and dried over anhydrous sodium sulfate. The solvent was distilled off under reduced pressure. The residue was purified by silica gel chromatography to obtain 0.1 g of the desired product as a light brown crystal. The yield was 13%.

Example 5

Synthesis of N-[2-(1,3-dimethylbutyl)-3-thienyl]-6-ethyl-3,4-dihydro-2H-pyran-5-carboxamide (Compound No. 1.8)

In a nitrogen atmosphere, 1.0 g of 3-amino-2-(1,3-dimethylbutyl)-thiophene was dissolved in 10 ml of methylene chloride. To the resulting solution, 5 ml of a 15% toluene solution of trimethylaluminium was dropwise added with stirring. After stirring for 10 minutes, a solution containing 1.0 g of methyl 6-ethyl-3,4-dihydro-2H-pyran-5-carboxylate in 5 ml of methylene chloride was dropwise added.

After stiring at room temperature for 12 hours, the reaction mixture was poured into a 5% aqueous hydrochloric acid solution and extracted with ethyl acetate. The organic layers was washed with a 5% aqueous hydrochloric acid solution, and successively saturated carbonate solution and saturated aqueous sodium chloride solution, and dried over anhydrous sodium sulfate. The solvent was distilled off under reduced pressure. The residue was purified by silica gel chromatography to obtain 0.3 g of the desired product as brown oil. The yield was 17%.

Example 6

Synthesis of N-[2-(l,3-dimethylbutyl)-3-thienyl]-6-methyl-2,3-dihydro-1,4-oxathiine-5-carboxamide (Compound No. 1.14)

In a nitrogen atmosphere, 0.45 g of 3-amino-2-(1,3-dimethylbutyl)-thiophene was dissolved in 5 ml of methylene chloride. To the resulting solution, 2.86 ml of a 15% toluene solution of trimethylaluminium was dropwise added with stirring. After stirring for 10 minutes, a solution containing 0.46 g of ethyl 6-methyl-2,3-dihydro-1,4-oxathiine-5-carboxylate in 3 ml of methylene chloride was dropwise added.

After strring at room temperature for 4 hours, the reaction mixture was poured into a 1N aqueous hydrochloric acid solution and extracted with ethyl acetate. The organic layers was washed with a saturated aqueous sodium hydrogen carbonate solution and successively saturated aqueous sodium chloride solution, and dried over anhydrous sodium sulfate. The solvent was distilled off under reduced pressure. The residue was purified by silica gel chromatography to obtain 0.44 g of the desired product as brown oil. The yield was 55%.

Reference Example 1

Synthesis of 3-amino-2-(1,3-dimethylbutyl)thiophene 1) 2-(1-Hydroxy-1,3-dimethylbutyl)-3-t-butoxycarbonylaminothiophene A tetrahydroflran solution of 2-methylpropylmagnesium bromide was prepared from 2.9 g of 2-methylpropyl bromide, 0.47 g of magnesium and 20 ml of tetrahydrofuran. The solution was cooled to 10° C., 10 ml of a tetrahydrofaran solution containing 1 g of 2-acetyl-3-t-butyloxycarbonyl-aminothiophene was dropwise added at 15° C. or less, stirred at room temperature for 2 hours, and a saturated aqueous ammonium chloride solution was dropwise added with cooling. The reaction mixture was extracted with ethyl acetate, washed with a saturated aqueous sodium chloride solution, and dried over anhydrous sodium sulfate. The solvent was distilled off under reduced pressure to obtain 1.2 g of the desired product. The yield was 98%.

2) 3-Amino-2-(1,3-dimethylbutyl)thiophene

After dissolving 1.2 g of 2-(1-hydroxy-1,3-dimethylbutyl)-3-t-butoxycarbonylaminothiophene in 10 ml of methylene chloride, 0.44 g of triethylsilane and 4.3 g of trifluoroacetic acid were added. The mixture was stirred at room temperature for 20 hours, neutralized with a saturated aqueous sodium hydrogen carbonate solution, and extracted with ethyl acetate. The organic layer was washed with a saturated aqueous sodium chloride solution and dried over anhydrous sodium sulfate. The solvent was distilled off under reduced pressure. The residue was purified by silica gel column chromatography to obtain 0.43 g of the desired product as a crystal. $^1$H-NMR(270 MHz, CDCl$_3$, δppm, J:Hz):0.89(3H, d,J=6.6), 0.90(3H,d,J=6.6), 1.23(3H,d,J=6.6),1.35–1.65(3H, m), 2.95(1H, sextet, J=6.6), 3.35(2H,brs), 6.55(1H,d,J=5.1), 6.95(1H,d,J=5.1)

Reference Example 2

Synthesis of 3-amino-2-isoprpylthiophene

1) Methyl 3-(t-butoxycarbonylamino)thophene-2-carboxylate

To a solution containing 10 g of methyl 3-amimothiophene-2-carboxylate and 7.72 g of triethylamine in 50 ml of methylene chloride, a solution containing 13.9 g of di-t-butylcarbonate in 20 ml of methylene chloride was dropwise added and thereafter a catalytic amount of 4-dimethylamino-pyridine was added. The mixture was stirred at room temperature for 5 hours, separated into two layers. The organic layer was washed with water and dried over anhydrous sodium sulfate.

After distilling off the solvent under reduced pressure, the precipitated crystal was filtered. The filtrate was purified by silica gel column chromatography to obtain 4.2 g of the desired product as a colorless crystal. $^1$H—NMR(270 MHz, CDCl$_3$, δppm, J:Hz): 1.52(9H,s), 3.88 (3H, s), 7.43 (1H,d, J=5.1), 7.88 (1H,d,J=5.1), 9.35(1H,brs)

2) 2-(1-Hydroxy-1-methyl)ethyl-3-(t-butoxycarbonylamino)thiophene

In a nitrogen atmosphere, 6.5 ml of a 3M-ether solution of methyl-magnesium bromide was diluted with 5 ml of tetrahydrofuran, cooled to 10° C. and a solution containing 1 g of methyl 3-(t-butoxycarbonylamino)thiphene-2-carboxylate in 5 ml of tetrahydrofuran was dropwise added. After stirring at room temperature for 3 hours, the reaction mixture was poured into an aqueous ammonium chloride solution and extracted with ethyl acetate. The organic layer was washed with a saturated aqueous sodium chloride solution and dried over anhydrous sodium sulfate. The solvent was distilled off under reduced pressure to obtain the desired product as yellow oil. The yield was theoretical. $^1$H-NMR(270 MHz, CDCl$_3$, δppm, J:Hz):1.50 (9H,s),1.65 (6H,s),7.02 (1H,d,J=5.1),7.27 (1H,d,J=5.1),8.09 (1H,brs)

3) 3-Amino-2-isopropylthiophene

After dissolving 0.9 g of 2-(1-hydroxy-1-methyl)ethyl-3-t-butoxycarbonylaminothiophene in 10 ml of methylene chloride, 0.41 g of triethylsilane and 4 g of trifluoroacetic acid were added. After stirring at room temperature for 20 hours, the reaction mixture was neutralized with a saturated aqueous sodium hydrogen carbonate solution, extracted with ethyl acetate. The organic layer was washed with a saturated aqueous sodium chloride solution, and dried over magnesium sulfate. After distilling off the solvent under reduced pressure, the residue was purified by silica gel column chromatography to obtain 0.29 g of the desired product as a crystal. The yield was 62%. $^1$H—NMR(270 MHz, CDCl$_3$, δppm, J:Hz):1.28(6H,d,J=7.3),3.04(1H,sept, J=7.3), 3.07(2H,brs),6.56 (1H,d,J=5.9),6.93(1H,d,J=5.9)

Other compounds represented by the formula (1) which were prepared by the same process as the examples were summarized in Table 1 and Table 2.

TABLE 1

(2-substituted-3-acylaminothiophene derivatives)

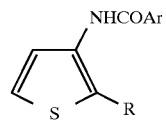

| Compound No. | R | Ar Substituent | m.p. (°C.) | $^1$H-NMR(270 MHz) (CDCl$_3$, δ value, J:Hz) |
|---|---|---|---|---|
| 1.1 | isopropyl | A1(R$^1$ = CF$_3$, R$^3$ = Cl) | | |
| 1.2 | 1-methyl-propyl | A2(R$^2$ = CF$_3$, m = 0) | | |
| 1.3 | 1-methyl-propyl | A4(R$^2$ = CF$_3$) | | |
| 1.4 | 1-ethyl-propyl | A1(R$^1$ = Me, R$^3$ = Cl) | | |
| 1.5 | 1-methyl-butyl | A1(R$^1$ = CF$_3$, R$^3$ = Me) | | |
| 1.6 | 1-methyl-butyl | A1(R$^1$ = CF$_3$, R$^3$ = Cl) | | |
| 1.7 | 1,3-dimethyl butyl | A2(R$^2$ = Me, m = 0) | 82.2–87.1 | 0.87(3H, d, J=5.9), 0.88 (3H, d, J=5.9), 1.27(3H, d, J=6.6), 1.41–1.57(3H, m), 1.94(2H, tt, J=6.6, 5.9), 2.19(3H, s), 2.35(2H, t, J=6.6), 3.02(1H, m), 4.05(2H, t, J=5.9), 6.87(1H,, brs), 7.08(1H, d, J=6.5), 7.36(1H, d, J=5.9) |
| 1.8 | 1,3-dimethyl butyl | A2(R$^2$ = Et, m = 0) | oil | 0.87(3H, d, J=5.9), 0.88 (3H, d, J=6.6), 1.13(3H, t, J=7.3), 1.26(3H, d, J= 6.6), 1.3–1.60 (3H, m), 1.92(2H, tt, J=5.1, J=6.6), 2.35 (2H, t, J=6.6), 2.57(2H, q, J=7.3), 3.01(1H, m), 4.04 (2H, t, J=5.1), 6.88(1H, brs), 7.08(1H, d, J=5.9), 7.37(1H, d, J=5.1) |
| 1.9 | 1,3-dimethyl | A1(R$^1$ = R$^3$ = Me) | | |

TABLE 1-continued (2-substituted-3-acylaminothiophene derivatives)

$$\text{structure: thiophene with NHCOAr at position 3 and R at position 2}$$

| Compound No. | R | Ar Substituent | m.p. (°C.) | $^1$H-NMR(270 MHz) (CDCl$_3$, δ value, J:Hz) |
|---|---|---|---|---|
| 1.10 | 1,3-dimethyl butyl | A1(R$^1$ = CF$_3$, R$^3$ = Cl) | semi-solid | 0.87(6H, d, J=6.6), 1.26(3H, d, J=6.6), 1.43–1.65(3H, m), 3.09(1H, m), 3.96(3H, s), 7.13(1H, d, J=5.1), 7.46 (1H, d, J=5.1), 7.46(1H, br, s) |
| 1.11 | 1,3-dimethyl butyl | A1(R$^1$ = Me, R$^3$ = Cl) | brown oil | 0.88(6H, d, J=5.9), 1.28 (3H, d, J=7.3), 1.43–1.59(3H, m), 2.52(3H, s), 3.11(1H, m), 3.85(3H, s), 7.13(1H, d, J=5.9), 7.48(1H, d, J=5.9), 7.65(1H, brs) |
| 1.12 | 1,3-dimethyl butyl | A1(R$^1$ = CHF$_2$, R$^3$ = Cl) | | |
| 1.13 | 1,3-dimethyl butyl | A3(R$^2$ = Me, n = 1) | yellow oil | 0.87(6H, m), 1.21(3H, d, J=6.6), 1.39–1.60(3H, m), 2.40 (3H, s), 2.89(1H, m), 3.09 (2H, m), 4.56(2H, m), 7.20 (2H, m), 7.27(1H, m), 7.64–7.80(1H, m), 8.23(1H, brs) |
| 1.14 | 1,3-dimethyl butyl | A3(R$^2$ = Me, n = 0) | oil | 0.89(6H, m), 1.28(3H, d, J=6.6), 1.40–1.57(3H, m), 2.28(3H, s), 2.99(2H, m), 3.05 (1H, m) 4.39–43(2H, m), 7.09 (1H, d, J=5.1), 7.40(1H, d, J=5.1), 7.73(1H, brs) |
| 1.15 | 1,3-dimethyl butyl | A4(R$^2$ = Et) | 71.0–77.9 | 0.89(6H, m), 1.14(3H, t, J=7.3), 1.27(3H, d, J=7.3), 1.36–1.56(3H, m), 2.77 (1H, q, J=7.3), 2.96(2H, t, J=9.5), 2.98(1H, m), 4.47(2H, t, J=9.5), 6.62(1H, brs) 7.08(1H, d, J=5.1), 7.43 (1H, d, J=5.1) |
| 1.16 | 1,3-dimethyl butyl | A4(R$^2$ = Me) | 92–95 | 0.89(6H, m), 1.27(3H, d, J=6.6), 1.39–1.55(3H, m), 2.27 (3H, s), 2.96(2H, t, J=9.5), 2.98(1H, m), 4.48(2H, t, J=9.5), 6.62(1H, brs), 7.08(1H, d, J=5.1), 7.41(1H, d, J=5.1) |
| 1.17 | 1,2-dimethyl butyl | A1(R$^1$ = CF$_3$, R$^3$ = Br) | | |
| 1.18 | tert-butyl | A1(R$^1$ = CF$_3$, R$^3$ = Cl) | | |
| 1.19 | 1,3-dimethyl pentyl | A1(R$^1$ = Cl, R$^3$ = Cl) | | |
| 1.20 | 1,3-dimethyl butyl | A2(R$^2$ = CF$_3$, m = 0) | 117.5–120.5 | 0.88(6H, m), 1.25(3H, d, J=6.6), 1.38–1.57(3H, m), 1.99 (2H, m), 2.50(2H, m), 3.04 (1H, m), 4.16(2H, t, J=5.1), 6.95(1H, brs), 7.11(1H, d, J=5.9), 7.30(1H, d, J=5.9) |
| 1.21 | 3-methyl butyl | A2(R$^2$ = Me, m = 0) | 122.1–122.4 | 0.93(6H, d, J=5.9), 1.49–1.66(3H, m), 1.89–1.98(2H, m), 2.19(3H, s), 2.33–2.37 (2H, m), 2.64–2.70(2H, m), 4.02–4.06(2H, m), 6.87 (1H, brs), 7.05(1H, d, J=5.1), 7.26(1H, d, J=5.1) |
| 1.22 | 1,3-dimethyl butyl | A4(R$^2$ = CF$_3$) | oil | 0.87(6H, d, J=5.9), 1.25 (3H, d, J=6.6), 1.41–1.57(3H, m), 3.02(1H, m), 3.22(2H, m), 4.59(2H, m), 7.10(1H, d, J=5.9), 7.11(1H, brs), 7.36 (1H, d, J=5.1) |

TABLE 1-continued (2-substituted-3-acylaminothiophene derivatives)

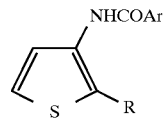

| Compound No. | R | Ar Substituent | m.p. (°C.) | $^1$H-NMR(270 MHz) (CDCl$_3$, δ value, J:Hz) |
|---|---|---|---|---|
| 1.23 | 1,2,2,3-tetramethyl-butyl | A5(R$^1$ = Br) | | |
| 1.24 | 1,3,3-tri-methylbutyl | A1(R$^1$ = CF$_3$, R$^3$ = Cl) | | |
| 1.25 | 1,3-dimethyl butyl | A5(R$^1$ = CF$_3$) | | |
| 1.26 | 1,3-dimethyl pentyl | A1(R$^1$ = CF$_3$, R$^3$ = Cl) | | |
| 1.27 | 5-methyl-3-hexyl | A4(R$^2$ = CF$_3$) | | |
| 1.28 | 2-methyl-4-heptyl | A4(R$^2$ =CHF$_2$) | | |
| 1.29 | 1-methyl-2-cyclopropyl-ethyl | A1(R$^1$ =CF$_3$, R$^3$ = Br) | | |
| 1.30 | 3-chloro-1-methylbutyl | A1(R$^1$ =CF$_3$, R$^3$ = Cl) | | |
| 1.31 | 2-chloro-1-methylbutyl | A1(R$^1$ = CF$_3$, R$^3$ = Cl) | | |
| 1.32 | 1-methyl-3-trifluoro-methylbutyl | A4(R$^2$ = CF$_3$) | | |
| 1.33 | 3-methyl-1-trifluoro-methylbutyl | A4(R$^2$ = CF$_3$) | | |
| 1.34 | 1,3-dimethyl butyl | A3(R$^2$ = Me, n = 2) | 86.5–92.0 | |
| 1.35 | 1,2-dimethyl butyl | A3(R$^2$ = Me, n = 1) | | |
| 1.36 | 1,3-dimethyl butyl | A5(R$^1$ = Me) | 79–81 | 0.86–0.90(6H, m), 1.29 (3H, d, J=6.6), 1.43–1.59(3H, m), 2.73(3H, s), 3.09(1H, m), 7.15(1H, d, J=5.9), 7.40 (1H, m), 8.94(1H, s) |
| 1.37 | 1,3-dimethyl pentyl | A4(R$^2$ = CF$_3$) | | |
| 1.38 | 1,3-dimethyl butyl | A2(R$^2$ = Me, m = 1, 3-Me) | 77–82 | 0.89(6H, m), 1.03(3H, d, J=6.6), 1.28(3H, d, J=6.6), 1.40–1.62(3H, m), 1.89–2.04 (2H, m), 2.20(3H, s), 2.44(1H, m), 3.03(1H, m), 3.53(1H, m), 4.05(1H, m), 6.86(1H, brs), 7.08(1H, d, J=5.9), 7.36 (1H, d, J=5.9) |
| 1.39 | 1,3-dimethyl butyl | A2(R$^2$ = Me, m = 1, 2-Me) | yellow oil | 0.88(6H, m), 1.27(3H, d, J=6.6), 1.33(3H, d, J=5.9), 1.40–1.68(3H, m), 1.64(1H, m), 1.95(1H, m), 2.20(3H, s), 2.35(2H, m), 3.02(1H, m), 3.97(1H, m), 6.87(1H, brs), 7.08(1H, d, J=5.9), 7.36(1H, d, J=5.9) |
| 1.40 | 1-chloro-3-methylbutyl | A4(R$^2$ = CF$_3$) | | |
| 1.41 | 3-methyl-cyclohexyl | A2(R$^2$ = Me, m = 0) | | |
| 1.42 | 1,3-dimethyl butyl | A1(R$^1$ = Et, R$^3$ = Cl) | 95.5–100 | 0.88(6H, d, J=5.9), 1.27 (6H, m), 1.43–1.58(3H, m), 2.95(2H, q, J=7.3), 3.11(1H, m), 3.86(3H, s), 7.12(1H, d, J=5.9), 7.46(1H, d, J=5.9), 7.62(1H, brs) |
| 1.43 | 1,3-dimethyl-1-butenyl | A1(R$^1$ = CF$_3$, R$^3$ = Cl) | | |

TABLE 1-continued (2-substituted-3-acylaminothiophene derivatives)

$$\underset{S}{\overset{NHCOAr}{\bigotimes}}R$$

| Compound No. | R | Ar Substituent | m.p. (°C.) | $^1$H-NMR(270 MHz) (CDCl$_3$, δ value, J:Hz) |
|---|---|---|---|---|
| 1.44 | 4-methyl cyclohexyl | A5(R$^1$ = CF$_3$) | | |
| 1.45 | 3-methyl-cyclohexyl | A5(R$^1$ = Cl) | | |

TABLE 2

(2-substituted-3-acylaminothiophene derivatives)

$$\underset{S}{\overset{R\quad NHCOAr}{\bigotimes}}$$

| Compound No. | R | Ar substituent | m.p. (°C.) | $^1$H-NMR(270 MHz) (CDCl$_3$, δ value, J:Hz) |
|---|---|---|---|---|
| 2.1 | 1-methyl-propyl | A1(R$^1$ = CF$_3$, R$^3$ = Me) | | |
| 2.2 | 1-methyl-butyl | A2(R$^2$ = Me, m = 0) | | |
| 2.3 | 1,3-dimethyl butyl | A2(R$^2$ = Me, m = 0) | | |
| 2.4 | 1,3-dimethyl butyl | A5(R$^1$ = CF$_3$) | | |

Next, formulation examples and test examples will be illustrated on the plant disease controlling agent of the invention. In the formulation example, "parts" means "parts by weight".

Formulation Example 1 (Powdwe Formulation)

A powder containing 2% by weight of an active ingredient was obtained by uniformly grinding and missing 2 parts of the compound having Compound No. 1.11 and 98 parts of clay.

Formulation Example 2 (Wettable Powder)

A wettable powder which had a uniform composition, was a pulverized particle, and contained 10% by weight of an active ingredient was obtained by uniformly grinding and mixing 10 parts of the compound having Compound No. 1.8, 70 parts of kaolin, 18 parts of white carbon, and 2 part of calcium alkylbenzenesulfonate.

Formulation Example 3 (Wettable Powder)

A wettable powder which had a uniform composition, was a pulverized particle, and contained 20% by weight of an active ingredient was obtained by uniformly grinding and mixing 20 parts of the compound having Compound No. 1.7, 3 parts of calcium alkylbenzenesulfonate, 5 parts of polyoxyethylene nonyl phenyl ether, and 72 part of clay.

Formulation Example 4 (Wettable Powder)

A wettable powder containing 50% by weight of an active ingredient was obtained by uniformly grinding and mixing 50 parts of the compound having Compound No. 1.14, 1 parts of sodium lignin sulfonate, 5 parts of white carbon, and 44 parts of diatomaceous earth.

Formulation Example 5 (Flowable Formulation)

A flowable formulation containing 5% by weight of an active ingredient was prepared by wet grinding with a sand grinder 5 parts of the compound having Compound No. 1.7, 7 parts of propylene glycol, 4 parts of sodium lignin sulfonate, 2 parts of sodium dioctylsulfosuccinate, and 82 parts of water.

Formulation Example 6 (Flowable Formulation)

A flowable formulation containing 10% by weight of an active ingredient was prepared by wet grinding with a sand grinder 10 parts of the compound having Compound No. 1.16, 7 parts by weight of propylene glycol, 2 parts of sodium lignin sulfonate, 2 parts of sodium dioctylsulfosuccinate, and 79 parts of water.

Formulation Example 7 (Flowable Formulation)

A flowable formulation containing 25% by weight of an active ingredient was obtained by wet grinding with a sand grinder 25 parts of the compound having Compound No. 1.42, 5 parts of propylene glycol, 5 parts of polyoxyethyl-eneoleate ester, 5 parts of polyoxyethylene diallyl ether sulfate, 0.2 parts of silicone-based antifoaming agent, and 59.8 parts of water.

The compounds of the invention will hereinafter be illustrated the activity as a plant disease controlling agent by way of test examples.

Test Example 1

Control test against gray mold (*Botrytis cinerea*) of kidney beans

In a green house, two seedlings of kidney beans (cultivar: Veinless Top Crop) were grown in each plastic pot having a diameter of 7.5 cm until development of cotyledon. A wettable powder which was prepared according to Formulation Example 3 was diluted to the prescribed concentration (active ingredient concentration of 100 and 200 ppm) and air dried after spraying on the seedlings with 50 ml portions per four pots.

A conidiospore suspension (1×10$^6$ spores/ml) was prepared from gray mold fungus (*Botrytis cinerea*, MBC resistant, RS strain) which was cultured on a PDA medium, and spray-inoculated on the cotyledon, and allowed to stay in a greenhouse at 20°–23° C. for 7 days under relative humidity of 95% or more.

After 7 days from the inoculation, the lesion area of Botrytis cinerea mold per leaf of kidney beans was examined on the basis of the following index. The grade of severity is shown by the index and the control value was calculated by the formula below. Results are illustrated in Table 3.

Severity 0: no lesion

1: lesion area is 5% or less

2: lesion area is 5–25%

3: lesion area is 25–50%

4: lesion area is 50% or more

The mean value of each treated area and untreated area is defined as severity.

Control value (%)=(1-severity in the treated area/severity in the untreated area)×100

TABLE 3

| Compound | Control Value (%) | |
| --- | --- | --- |
| No. | 200 ppm | 100 ppm |
| 1.7 | 100 | 100 |
| 1.8 | 100 | 100 |
| 1.11 | 100 | 100 |
| 1.14 | 100 | 100 |
| 1.16 | 100 | 100 |
| 1.21 | 100 | 100 |
| Ref. Compd. 1 | 100 | 32 |
| Ref. Compd. 2 | 100 | 10 |

Note: Reference compounds were described in EP-A-737682

Ref. Compd. 1: N-(1,3-dimethylbutyl)-3-thienyl-2-chloronicotinic acid amide.

Ref. Compd.2: N-(1,3-dimethylbutyl)-3-thienyl-o-toluic acid amide.

Test Example 2

Control test against cucumber powdery mildew

In a green house, two seedlings of cucumber (cultivar: Sagami Hanjiro) were grown in each plastic pot having a diameter of 7.5 cm until the 1.5 leaf stage. A wettable powder which was prepared according to Formulation Example 3 was diluted to the prescribed concentration (active ingredient concentration of 100 and 200 ppm) and air dried after spraying on the seedlings with 50 ml portions per three pots.

A conidiospore suspension (1×10$^6$ spores/ml) was prepared by suspending conidiospore of cucumber powdery mildew fungus in water which contains a small amount of spreader, and spray-inoculated on the leaf, and allowed to stay in a greenhouse for 7 days.

After 7 days from the inoculation, the lesion area of powdery mildew per leaf of cucumber was examined on the basis of the index described in Test Example 1. The grade of severity is shown by the index and the control value was calculated by the formula below. Results are illustrated in Table 4.

Control value (%)=(1-severity in the treated area/severity in the untreated area)×100

TABLE 4

| Compound | Control Value (%) | |
| --- | --- | --- |
| No. | 200 ppm | 100 ppm |
| 1.7 | 100 | 100 |
| 1.11 | 100 | 100 |
| 1.14 | 100 | 100 |
| 1.21 | 100 | 100 |
| 1.36 | 100 | 100 |
| 1.42 | 100 | 100 |
| Ref. Compd. 2 | 100 | 30 |

Test Example 3

Control test against Pyricularia oryzae of rice plant

In a green house, 40–50 seedlings of rice plant (breed: Mangetsumochi) were grown in each pot until the two leaf stage. A wettable powder which was prepared according to Formulation Example 3 was diluted to the prescribed concentration (active ingredient concentration of 100 and 200 ppm) and sprayed on the seedlings by 50 ml portions per three pots.

After the sprayed chemical was dried, a conidiospore suspension (4×10$^5$ spores/mil) was prepared from Pyricularia oryzae which was cultured on an oatmeal medium and spray-inoculated over the whole surface of seedlings. Thus treated seedlings were allowed to stay in a plant growth chamber at temperature of 25° C. under relative humidity of 95% or more for 8 days.

After 8 days from the inoculation, the lesion number of Pyricularia oryzae per five seedlings of rice plant was assessed on the basis of the following index and a control value was obtained according to the below described formula. Results are illustrated in Table 5.

Severity 0: no lesion

1: 1–2 lesions

2: 3–5 lesions

3: 6–10 lesions

4: 11 or more lesions

The mean value of each treated area and untreated area is defined as severity.

Control value (%)=(1-severity in the treated area/severity in the untreated area)×100

TABLE 5

| Compound | Control Value (%) | |
| --- | --- | --- |
| No. | 200 ppm | 100 ppm |
| 1.7 | 100 | 100 |
| 1.11 | 100 | 100 |
| 1.14 | 100 | no test |
| 1.16 | 100 | no test |
| 1.21 | 100 | 100 |
| Ref. Compd. 1 | 100 | 32 |
| Ref. Compd. 2 | 100 | 10 |

Test Example 4

Control test against wheat brown rust

In a green house, 15–20 seedlings of wheat (cultivar: Norin NO. 61) were grown in each plastic pot having a diameter of 6 cm until the 1.5 leaf stage. A wettable powder which was prepared according to Formulation Example 3 was diluted to the prescribed concentration and air dried after spraying on the seedlings with 50 ml portions per three pots.

Thus treated seedlings were successively sprayed with summer spore of wheat brown rust fungus (*Puccinia recondita*), allowed to stand in a moist condition for 2 days and transferred to a room which was maintained at 18° C.

After 10 days from the inoculation, the lesion area of brown rust on the primary leaf of wheat was examined to obtain a minimum inhibitory concentration. Inspection of severity and calculation of control value were carried out by the same method as Test Example 1. Results are illustrated in Table 6.

TABLE 6

| Compound No. | Minimum Inhibitory concentration (ppm) |
|---|---|
| 1.7 | 0.5 |
| 1.21 | 1.0 |
| Reference Compound 1 | 10 |
| Reference Compound 2 | 18 |

Text Example 5

Test on residual effect against *Botrytis cinerea* of string beans

In a green house, two seedlings of kidney beans (breed: Veinless top crop) were grown until development of cotyledon in each plastic pot having a diameter of 7.5 cm. A wettable powder which was prepared according to Formulation Example 3 was diluted to a prescribed concentration (active ingredient concentration of 200 ppm) and sprayed by 80 ml portion per three pots. After the prescribed days from spraying, one cotyledon was individually cut from each pot.

A conidiospore suspension ($1 \times 10^6$ spore/ml) was prepared from (MBC resistant, RS strain) which was previously cultured on a PDA medium, and was absorbed on a paper disc having a diameter of 8 mm.

Inoculation was carried out by placing the paper disc on the above cotyledon. After allowing to stay in a green house at 20° C. under relative humidity of 95% or more for 4 days, the diameter of lesion of *Botrytis cinerea* was measured. Control value was calculated from the equation below on the basis of the measured values. Results are illustrated in Table 7.

Control value (%)=(1-severity in the treated area/severity in the untreated area)×100

TABLE 7

| | Control Value (%) | | |
|---|---|---|---|
| Compound No. | 2 days | 6 days | 9 days |
| 1.7 | 100 | 100 | 100 |
| 1.21 | 100 | 100 | 95 |
| Ref. Compd. 1 | 60 | 8 | 5 |
| Ref. Compd. 2 | 40 | 15 | 0 |

What is claimed is:

1. A substituted thiophene derivative represented by the formula (1):

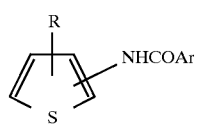

wherein R is a straight or branched alkyl group having 3–12 carbon atoms, straight or branched halogenoalkyl group having 3–12 carbon atoms, straight or branched alkenyl group having 3–10 carbon atoms, straight or branched halogenoalkenyl group having 3–10 carbon atoms, or cycloalkyl group having 3–10 carbon atoms, the cycloalkyl group being unsubstituted or substituted with an alkyl group having 1–4 carbon atoms, R and —NHCOAr are adjacent to each other, and Ar is a heterocyclic group represented by the formulas (A1)–(A5):

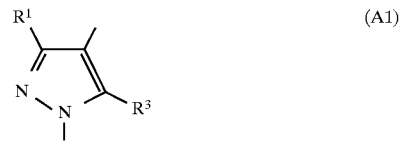

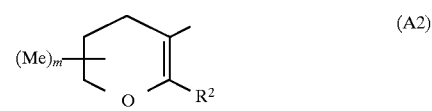

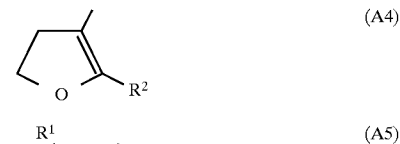

wherein $R^1$ is a trifluoromethyl group, difluoromethyl group, methyl group, ethyl group or halogen atom, $R^2$ is a methyl group, ethyl group, trifluoromethyl group or difluoromethyl group, $R^3$ is a halogen atom, methyl group or methoxy group, m is an integer of 0–1, and n is an integer of 0–2.

2. The substituted thiophene derivative according to claim 1, wherein R is a straight or branched alkyl group having 5–7 carbon atoms.

3. The substituted thiophene derivative according to claim 2, wherein R is a 1,3-dimethylbutyl group or 3-methylbutyl group.

4. The substituted thiophene derivative according to claim 3, wherein Ar is (A1), $R^1$ is a methyl group, and $R^3$ is a halogen atom.

5. The substituted thiophene derivative according to claim 3, wherein Ar is (A2), $R^2$ is methyl group or ethyl group, and m is 0.

6. The substituted thiophene derivative according to claim 5, wherein $R^2$ is methyl group.

7. The substituted thiophene derivative according to claim 3, wherein Ar is (A3), $R^2$ is methyl group, and n is 0.

8. The substituted thiophene derivative according to claim 3, wherein Ar is (A4), $R^2$ is methyl group.

9. A plant disease control agent comprising the substituted thiophene derivative according to claim 1 as an active ingredient.

10. The plant disease control agent comprising the substituted thiophene derivative according to claim 2 as an active ingredient.

11. The plant disease control agent comprising the substituted thiophene derivative according to claim 3 as an active ingredient.

12. The plant disease control agent comprising the substituted thiophene derivative according to claim 4 as an active ingredient.

13. The plant disease control agent comprising the substituted thiophene derivative according to claim 5 as an active ingredient.

14. The plant disease control agent comprising the substituted thiophene derivative according to claim 6 as an active ingredient.

15. The plant disease control agent comprising the substituted thiophene derivative according to claim 7 as an active ingredient.

16. The plant disease control agent comprising the substituted thiophene derivative according to claim 8 as an active ingredient.

* * * * *

UNITED STATES PATENT AND TRADEMARK OFFICE
CERTIFICATE OF CORRECTION

PATENT NO. : 5,869,427
DATED      : February 9, 1999
INVENTOR(S): Yukihiro Yoshikawa, et. al.

It is certified that error appears in the above-identified patent and that said Letters Patent is hereby corrected as shown below:

Title page, item [30], should read --
November 6, 1996    Japan    8-293684

In claim 1, column 26, line 36, delete "trriluoromethyl" and insert -- trifuoromethyl--

Signed and Sealed this

Twenty-fifth Day of January, 2000

Attest:

Attesting Officer

*Acting Commissioner of Patents and Trademarks*